United States Patent [19]

Graeber et al.

[11] Patent Number: 4,859,778

[45] Date of Patent: Aug. 22, 1989

[54] PROCESS FOR THE PREPARATION OF 2,2'-DITHIOBIS (BENZOTHIAZOLE)

[75] Inventors: Edward L. Graeber, Spring City; Michael J. Lindstrom, Downington, both of Pa.

[73] Assignee: Pennwalt Corporation, Philadephia, Pa.

[21] Appl. No.: 169,258

[22] Filed: Mar. 17, 1988

[51] Int. Cl.$^4$ .......................................... C07D 417/12
[52] U.S. Cl. .................................................... 548/158
[58] Field of Search ........................................ 548/158

[56] References Cited

U.S. PATENT DOCUMENTS

| | | |
|---|---|---|
| 1,631,871 | 6/1927 | Kelly ................................ 260/306.5 |
| 2,349,599 | 5/1944 | Moorhouse ....................... 260/306.5 |
| 2,730,528 | 1/1956 | Weyker et al. ....................... 260/306 |
| 2,830,058 | 4/1955 | Young .................................... 548/158 |
| 3,033,876 | 5/1962 | Blose .................................... 548/158 |
| 3,131,196 | 4/1964 | Wood .................................... 260/306 |
| 4,337,344 | 6/1982 | Alicot et al. ......................... 548/158 |
| 4,482,720 | 11/1984 | Kaplan et al. ........................ 548/158 |
| 4,755,607 | 7/1988 | Gaser .................................... 548/158 |

Primary Examiner—Robert Gerstl

[57] ABSTRACT

An improved process for the manufacture of 2,2'-dithiobis(benzothiazole). More particularly, the invention relates to an improved process for preparing 2,2'-dithiobis(benzothiazole) using various nonionic and cationic surfactants to reduce or eliminate the formation of large particles in the product.

9 Claims, No Drawings

PROCESS FOR THE PREPARATION OF 2,2'-DITHIOBIS (BENZOTHIAZOLE)

BACKGROUND OF THE INVENTION

This invention relates to the use of various nonionic and cationic surfactants during the preparation of 2,2'-dithiobis (benzothiazole) to reduce or eliminate the formation of large particles in the product.

The production of 2-mercaptobenzothiazole (a starting material for the production of 2,2'-dithiobis (benzothiazole)) from aniline, carbon disulfide and sulfur, as described by Kelly in U.S. Pat. No. 1,631,871, is accompanied by the production of unwanted tarry by-products. As part of the purification process, the crude mercaptobenzothiazole is dissolved in caustic solution, thereby effecting formation of the sodium salt of mercaptobenzothiazole. However, many of these by-products pass into the aqueous caustic solution either as salts or as dissolved impurities. During the chlorine/air oxidation of this solution to form 2,2'-dithiobis(benzothiazole), tarry droplets and large agglomerates form as a result of the presence of these impurities, along with the desired product. These particles and agglomerates are known in the art as "sand" and are fairly large in size in relation to the particles of the reaction product. The presence of this "sand" causes problems when the benzothiazole is compounded into rubber stock as a vulcanization accelerator. Physical removal of some of these particles is possible by sieving but this requires extra processing steps and significant amounts of 2,2'-dithiobis(benzothiazole) contained in the "sand" are removed and subsequently must be recycled in some manner.

Therefore, a process in which 2,2'-dithiobis (benzothiazole) is produced with uniform particle size is desirable.

U.S Pat. No. 2,830,058 discloses that sand formation is reduced or eliminated if anionic surfactants, like sodium stearate, are present at concentrations of 1 to 15% during the oxidation of mercaptobenzothiazole to benzothiazolyl disulfide. Furthermore, the patent asserts that nonionic and cationic surfactants appear to be substantially inactive for this purpose.

SUMMARY OF THE INVENTION

This invention is directed to an improved process of preparing 2,2'-dithiobis(benzothiazole) by the oxidation of an aqueous solution of sodium mercaptobenzothiazole with a mixture of chlorine and air in the presence of a cationic or nonionic surfactant at a temperature between about 25° C. and about 75° C. The resulting product contains a minimum of "sand" formation.

DESCRIPTION OF THE INVENTION

We have found that cationic and nonionic surfactants are effective in reducing or eliminating "sand" formation when present during the oxidation of sodium mercaptobenzothiazole to 2,2'-dithiobis(benzothiazole) with a mixture of chlorine and air.

The term surfactant refers to those classes of compounds which are typically used as wetting agents, emulsifiers, detergents and dispersing agents like sodium salts of fatty acids, polyethylene glycol ethers or ethoxylated long-chain amines. Surfactants are commercially available under various trade names. This process is effective with nonionic and cationic surfactants such as Tergitol ® 25-L-3, Pluronic ® L-43 and Trymeen ® 6607 TAM-20. The preferred surfactant is Trymeen ® 6607 TAM-20, a mildly cationic agent from Emery Industries.

An aqueous solution of sodium mercaptobenzothiazole is prepared by diluting a commercially prepared 15% by weight solution. A 5–10% by weight solution is normally used with a 10% solution being preferred.

The solution is oxidized in the presence of a mixture of air and chlorine introduced at a ratio of from 20:1 to 240:1 by volume. The higher air/$Cl_2$ ratios are preferred. The reaction should be conducted as slowly as possible but still maintain a commercially viable production rate.

The reaction temperature employed may be between about 25° C. and about 75° C. The preferred range for the invention is between about 40° C. and 65° C. with the most preferred temperature being 65° C. The reaction temperature is controlled by external heating or cooling.

The pH of the reaction of the reaction mixture is normally kept in the range of 9.0 to 12.0, preferably near 10, by the addition of caustic. At pH's below 9, there is some unwanted precipitation of mercaptobenzothiazole, while above pH 12, there is a decrease in yield of the reaction product.

The surfactant is added from about 0.01 to about 15% by weight based on the weight of the solution. It is preferred to use no more than about 1% by weight of the surfactant because using a greater amount can result in unnecessary foaming.

The following specific examples further illustrate the invention but are not intended to be limiting. All parts are by weight unless otherwise noted. For simplicity, the following abbreviations will be used:
MBT—mercaptobenzothiazole
MBTS—2,2'-dithiobis(benzothiazole)
—Sodium mercaptobenzothiazole The examples show that the percentage of large particles in the product are significantly reduced or eliminated by the use of nonionic or cationic surfactants. In particular, the use of 0.1% Trymeen ® 6607 TAM-20 in a 65° C. solution, as shown in Table 3, virtually eliminate any large particles in the product even on the 45 micron mesh.

DEFINITIONS OF SURFACTANTS USED IN THE EXAMPLES

Tergitol ® 25-L-3 is a nonionic, polyethylene glycol ether of a primary alcohol from Union Carbide of the formula: $RO(CH_2CH_2O)_a$—H where R is $C_{12}$–$C_{15}$ linear alcohol and $a = 3$ which is the average number of ethylene oxide units.

Pluronic ® L-43 is a nonionic, block co-polymer of ethylene and propylene oxide from BASF Co. of the formula:

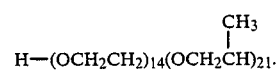

Trymeen ® 6607-TAM20 is a mildly cationic ethoxylated fatty amine from Emery Industries, Inc. of the formula:

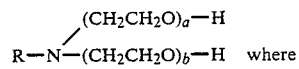

where

R=$C_{12}$–$C_{18}$ alkyl and a+b=20, which is the average moles of combined ethylene oxide per mole of amine.

EXAMPLE 1

To 465.9 grams of an aqueous solution of NaMBT, the solution containing 10.8% by weight of MBT, was added 38.9 g of distilled water to bring the MBT concentration of the solution to 10% by weight. The solution was contained in a one liter resin flask equipped with an anchor-type mechanical stirrer and sub-surface gas inlet tube. The solution was brought to 40° C. and the pH was adjusted to 10 by the addition of 25.4% NaOH solution. Additionally, 0.05g (0.01% by weight), Trymeen 6607 TAM-2 was added to the NaMBT solution. A vigorous stirring rate was maintained while a mixture of air and $Cl_2$ in a ratio of 20:1 was introduced. The pH of the solution was maintained at 10.0 by the intermittent addition of 25.4% NaOH. The progress of the reaction was monitored by a platinum electrode constantly recording the millivolt potential of the reaction mixture. Upon addition of the first portions of air/$Cl_2$, large, tarry, agglomerates form which were eventually followed by the formation of finer particles. The reaction's endpoint was reached when a relative millivolt oxidation potential of −100 mv is obtained. At this point, the gas flow was stopped and the reaction mixture was stirred for an additional ten minutes at 65° C. and pH at 10. The slurry was then cooled to 25° C. in an ice water bath and the product was filtered and collected in a Buchner funnel. It was washed with tap water until the filtrate was neutral and dried in an oven at 65° C. for 16 hours. A yield of 46 g was obtained with the sieve residues as reported in Table 1. This procedure was repeated without the addition of a surfactant. A yield of 48.2 g was obtained and the sieve residues are reported in Table 1, along with results from Examples 2 and 3. The U.S. alternate series designation was used for the sieves with 325=45 microns.

TABLE 1

| Example | % product retained (on indicated mesh sieve) | | | |
|---|---|---|---|---|
| | 45 | 100 | 170 | 325 |
| 1 | 6.7 | 8.4 | 10.2 | 13.9 |
| Without surfactant | 7.9 | 21.9 | 32.7 | 43.5 |
| 2 | 9.2 | 13.4 | 16.6 | 22.1 |
| 3 | 10.0 | 11.7 | 14.1 | 17.3 |

EXAMPLE 2

The process of Example 1 was repeated except that (0.1% by weight) of Pluronic L-43 was added as the surfactant to the NaMBT solution prior to oxidation. A yield of 46 g was obtained. The sieve residues are reported in Table 1.

EXAMPLE 3

The procedure of Example 1 was repeated except that 0.5 g (0.1% by wt.) of Tergitol 25-L-3 surfactant was added to the solution prior to oxidation. A yield of 45 g was obtained. The sieve residues are reported in Table 1.

TABLE 2

| Example | % Product Retained (on indicated mesh sieve) | | | |
|---|---|---|---|---|
| | 45 | 100 | 170 | 325 |
| 4 | N.F. | 0.8 | 2.3 | 4.5 |
| Without surfactant | 13.4 | 32.5 | 45.0 | 61.7 |

(N.F. = none found)

EXAMPLE 4

The procedure of Example 1 was repeated except that the temperature of the solution was brought to 65° C. before the pH was adjusted to 10 and before the introduction of the air/$Cl_2$ mixture. 0.5 g (0.1% by wt.) of Trymeen 6607 TAM-20 was added to the NaMBT solution before the oxidation. The 65° C. temperature was maintained throughout the entire reaction. A yield of 46 g was obtained with the sieve analysis reported in Table 2. This procedure was repeated without the addition of a surfactant and a yield of 45.5 g of product was obtained. The sieve residues for this are also reported in Table 2.

Table 3 reports additional examples of MBTS preparation run with 0.1% TAM-20 and with differing air/$Cl_2$ ratios or MBT concentrations.

TABLE 3

| | MBTS PREPARATION | | | |
|---|---|---|---|---|
| | % Product Retained (on indicated mesh sieve) | | | |
| Conditions[1] | 45 | 100 | 170 | 325 |
| No surfactant | 13.4 | 32.5 | 45.0 | 61.7 |
| +0.1% TAM-20 | NF | 0.8 | 2.3 | 4.5 |
| 5% MBT conc +0.1% TAM-20 | NF | 1.1 | 2.6 | 4.5 |
| 150 mL/min $Cl_2$ 6/liter/min Air +0.1% TAM-20 | 0.1 | 1.1 | 2.0 | 2.9 |
| 225 mL/min $Cl_2$ 9 liter/min Air +0.1% TAM-20 | NF | 0.75 | 1.7 | 2.8 |

[1]10% MBT, 65° C., pH 10, 300 mL/min $Cl_2$, 6 liter/min air unless otherwise noted.

What is claimed is:

1. A process for preparing 2,2'-dithiobis (benzothiazole) which comprises contacting an aqueous solution of sodium mercaptobenzothiazole with a mixture of chlorine and air at a pH maintained in the range of 9.0 to 12.0 in the presence of a nonionic or cationic surfactant at a temperature between about 25° C. and about 75° C. and recovering precipitated 2,2'-dithiobis (benzothiazole) from said solution.

2. The process of claim 1 wherein the temperature is maintained at 65° C. throughout the reaction.

3. The process of claim 2 wherein the pH is controlled at about 10.

4. The process of claim 1 wherein the concentration of surfactant is from about 0.01 to about 1% by weight with respect to the solution.

5. The process of claim 1 wherein the surfactant is nonionic.

6. The process of claim 1 wherein the surfactant is cationic.

7. The process of claim 6 wherein the surfactant is an ethoxylated fatty amine of the formula

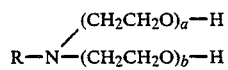

where B is $C_{12}$–$C_{18}$ alkyl and a+b, the average moles of combined ethylene oxide per mole of amino is 20.

8. The process of claim 5 wherein the surfactant is a nonionic, block co-polymer of ethylene and propylene oxide of the formula

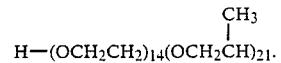

9. The process of claim 5 wherein the surfactant is a nonionic, polyethylene glycol of a primary alcohol of the formula $RO(CH_2CH_2O)_a$—H where R is $C_{12}$–$C_{15}$ linear alcohol and a, the average number of ethylene units is 3.

* * * * *